United States Patent [19]

Thompson

[11] Patent Number: 5,041,792

[45] Date of Patent: Aug. 20, 1991

[54] ELECTRODES INCORPORATING INTERCALATION COMPOUNDS FOR MANGETOTELLURIC, ELECTROSEISMIC AND OTHER ELECTRICAL SURVEY APPLICATIONS

[75] Inventor: Arthur H. Thompson, Houston, Tex.

[73] Assignee: Exxon Production Research Company, Houston, Tex.

[21] Appl. No.: 497,354

[22] Filed: Mar. 22, 1990

[51] Int. Cl.⁵ ............................................. G01V 3/08
[52] U.S. Cl. .................................................. 324/350
[58] Field of Search ......................... 324/323, 346–350

[56] References Cited

U.S. PATENT DOCUMENTS 4,237,204 12/1980 Thompson et al. .
4,632,732 12/1986 Fog et al. .
4,797,192 1/1989 Takiguchi .
4,862,089 8/1989 Sigal .................................... 324/350

OTHER PUBLICATIONS

"Some Aspects of Electrical Prospecting Applied in Locating Oil Structures", Leo J. Peters and John Bardeen, 2 *Physics*, pp. 103–122 (1932).
*Electrons and Holes in Semiconductors*, William Shockley, pp. 95–101, D. Van Nostrand Company, Inc. (1950).
"Fluctuation Spectroscopy: Determination of Chemical Reaction Kinetics from the Frequency Spectrum of Fluctuations", George Feher and Mike Weissman, 70 *Proc. Nat. Acad. Sci. U.S.A.*, No. 3, pp. 870–875 (Mar. 1973).
"Excess Electrical Noise During Current Flow Through Porous Membranes Separating Ionic Solutions", Douglas L. Dorset and Harvey M. Fishman, 21 *J. Membrane Biol.*, pp. 291–309 (1975).
"Diffusion and 1/f Noise", Michael E. Green, 28 *J. Membrane Biol.*, pp. 181–186 (1976).
"Noise, Temperature Coefficient, and Long Time Stability of Electrodes for Telluric Observations", G. Petiau and A. Dupis, 28 *Geophysical Prospecting*, pp. 792–804 (1980).
"Superionic Conduction", A. H. Thompson, *McGraw-Hill Encyclopedia of Science and Technology* (1981).
"Sodium Ion Conduction in Single Crystal Vermiculite", M. Stanley Whittingham, 25 *Solid State Ionics*, pp. 295–300 (1987).

Primary Examiner—Walter E. Snow
Attorney, Agent, or Firm—Vaden, Eickenroth, Thompson & Boulware

[57] ABSTRACT

A low noise, magnetotelluric, intercalation electrode is disclosed that is both electronically and ionically conductive and stable in ground water brine. The electrode is comprised of an inert or chemically inactive long cylindrical and porous support shield, a semipermeable membrane located in the shield selectively permeable to the positive ions of a metal selected from the group consisting of Na+ and K+ ions, a brine electrolyte, and an electrode axis located in the brine electrolyte that includes an electronically conductive, metallic material ionically reversible to Na+ and K+. The electrode is sealed and attachable at its electrode axis to a wire leading to another electrode spaced apart therefrom. The wire connection permits voltage measurements and thereby provides a method for determining the resistivity between the electrodes at frequencies that are quite low without being interferred with by noise attendant prior art magnetotelluric electrodes. Thus, such electrodes allow meaningful resistivity measurements not previously obtainable.

23 Claims, 2 Drawing Sheets

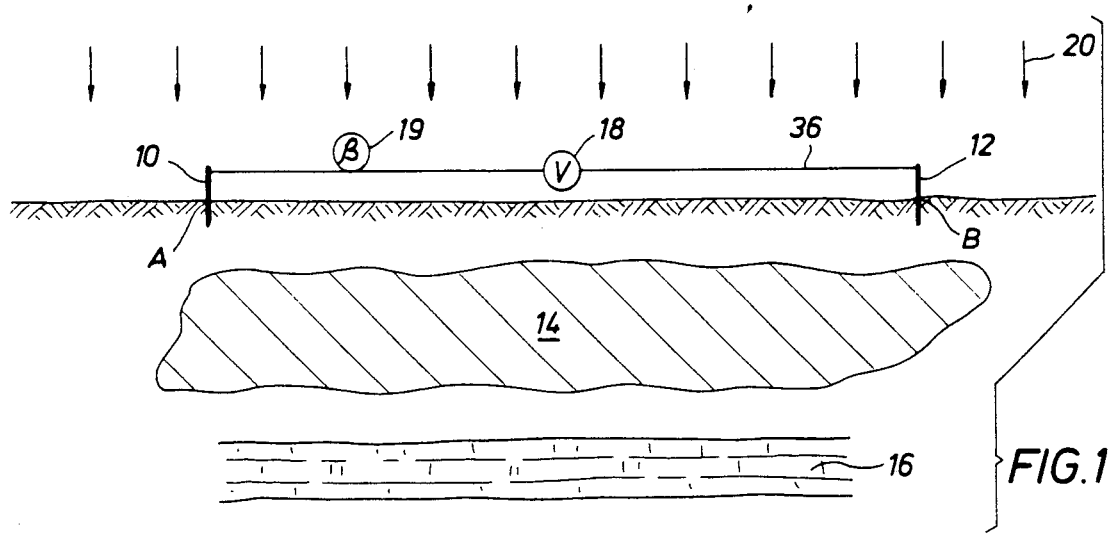
FIG.1
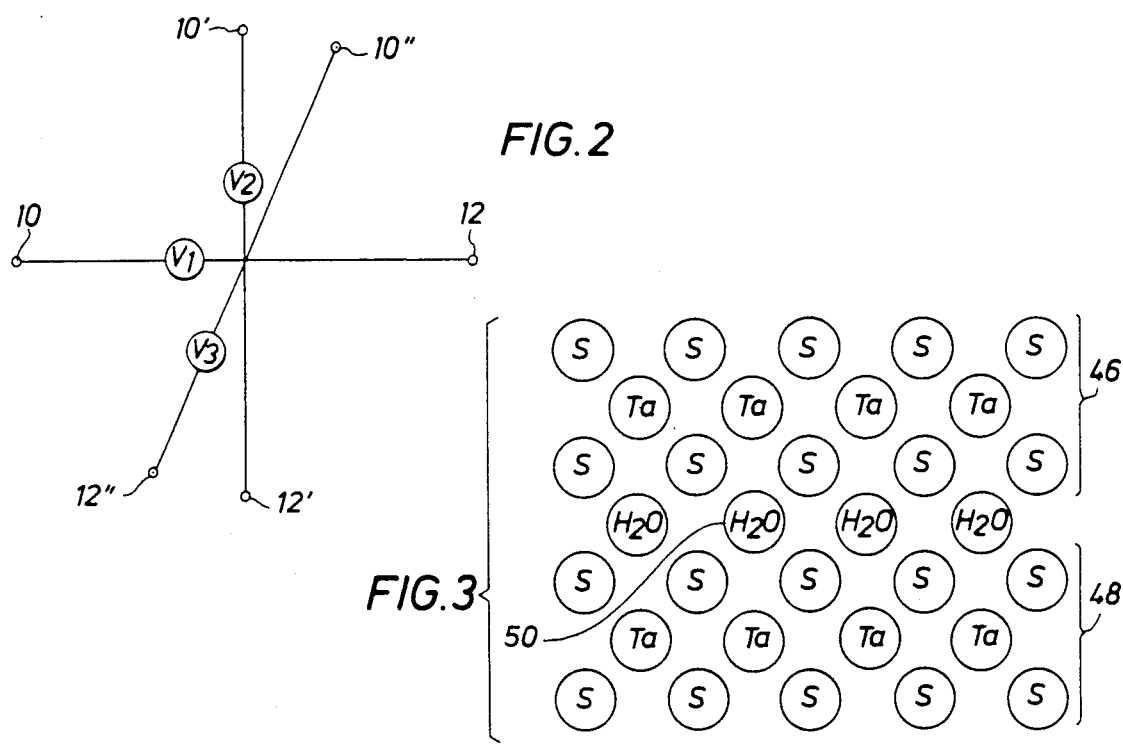
FIG.2
FIG.3
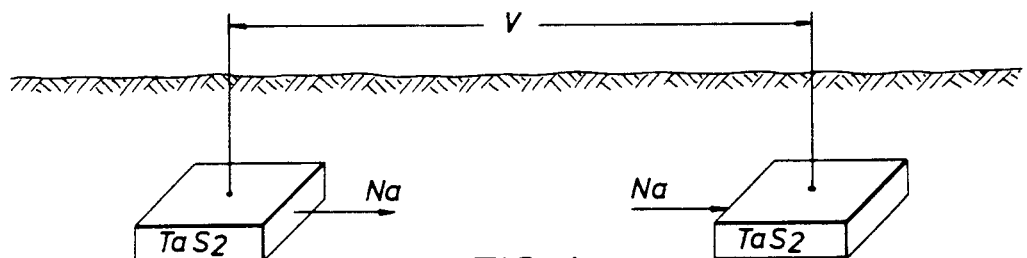
FIG.4

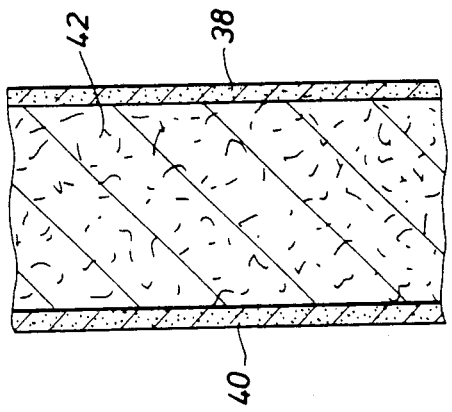
FIG. 6
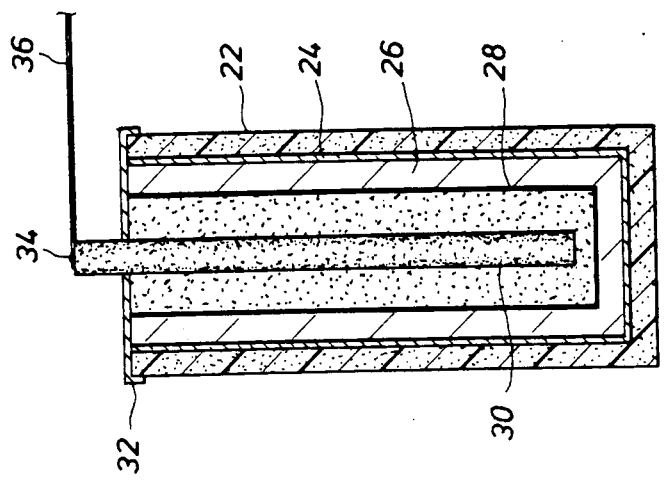
FIG. 5
FIG. 7

ELECTRODES INCORPORATING INTERCALATION COMPOUNDS FOR MANGETOTELLURIC, ELECTROSEISMIC AND OTHER ELECTRICAL SURVEY APPLICATIONS

BACKGROUND OF THE INVENTION

1. Field of the Invention

This invention pertains to electromagnetic surveying and to electrodes useful in magnetotelluric applications, especially in the environment of low frequency reception.

2. Description of the Prior Art

It is well-known that electromagnetic fields impinge on the earth's surface at all times and create both electrical fields and magnetic fields that are detectable utilizing proper techniques and apparatus.

Electric field and magnetic field detection at spaced apart locations can be important in electrical conductivity measurements for many applications. One important application is for making electromagnetic measurements useful in surveying for presence of hydrocarbon deposits located beneath very dense and rigid lithographic structures. For example, an oil or gas deposit located beneath a granite structure is virtually impossible to detect using conventional seismic techniques, but is detectable by measuring the voltage across two electrodes or "antennas" distantly placed. A typical electric dipole antenna electrode structure used in electromagnetic surveying comprises two electrodes buried in the ground and connected to wires that are fed to an electrometer amplifier for measuring voltage. In such a system there is an electronic-to-ionic contact between the electrodes of the antenna pair and the brines in the ground. Noise studies have been made on these antennas by G. Petian and A. Dupis, as reported in 28 *Geophysical Prospecting* at page 792 (1980) and indicate that the antenna noise is dominated by the electrode noise at frequencies below 1 Hz. This frequency limitation is important since high penetration or large depth studies can only be conducted at low frequencies. At higher frequencies, the electrical/ionic conducting barrier at the electrodes is small. However, at low frequency, the ions accumulate at a metallic electrode and create a very noisy electrode.

One approach to reducing noise is to use a solid metal that has a large surface area for slow ionic build up. A lead sheet of approximately one square foot area has been employed by being buried in the ground, connected to the antenna wire by an alligator clip, then saturated with a saline solution and stabilized for a day before measurements are made. This arrangement, although cumbersome, has allowed magnetotelluric measurements down to frequencies as low as $10^{-3}$ Hz. However, the area cannot be increased without limit because there are irreversible hydration or oxidation reactions that will eventually fully oxidize such a high-surface-area metal electrode. This oxidation will itself induce electrical noise.

A second type of electrode that has been used is the $Cu-CuSO_4$ "pot", comprising a copper wire in an electrolyte of $CuSO_4$ contained in a porous "pot" of inert material through which the ground water seeps. The observed noise of this type electrode is associated with current flow and appears to be in the charge flow across the metal-to-electrolyte interface and between the electrolyte and the ground water located in the wall pores of the porous pot.

None of the prior art structures that are known have low noise operating characteristics satisfactory for very low frequency application as hereinafter described.

Therefore, it is a feature of the present invention to provide an improved electrode for low frequency magnetotelluric use that is large in area and made of materials that are both electronically and ionically conducting and that are chemically compatible to the high salinity compounds found in solution in soils and stable therein.

It is another feature of the present invention to provide an improved method of making electrical conductivity measurements using the type of individual electrode described below.

It is still another feature of the present invention to provide an improved electrode of the type described below wherein the electronically and ionically conducting materials includes an intercalation or insertion compound.

SUMMARY OF THE INVENTION

One aspect of the invention described herein is a method of magnetotelluric surveying employing at least one pair of low noise, magnetotelluric, intercalation electrodes that are both electronically and ionically conductive and stable in ground water brine. The two electrodes are inserted into the ground at a distance from each other in the range of from only a few feet or meters to several thousand. They are then connected above ground to a voltage sensing element sensitive to frequencies below 1 Hz. Although this measurement alone is valuable, the same or different electrodes are driven into the ground at the same distance apart at one or more rotation positions and new measurements are taken at each rotation position, thereby determining not only an absolute value but the direction of maximum and minimum potential. These measurements can be evaluated for field strength and shape. If magnetic field measurements are taken simultaneously with the voltage measurements, then resistivity values between and below the electrodes can also be calculated.

An electrode in accordance with the present invention preferably includes a long cylindrical porous support shield that is electrically and ionically inactive. The shield encloses a cylindrical membrane that is semipermeable. That is, it is preferably selectively permeable to positive $Na+$ and $K+$ ions. The membrane is charged with a brine electrolyte that is preferably closely matched to the naturally occurring brine of the ground water existing at the use location. An electrode axis is located within the brine electrolyte, the axis being of an electronically conductive, metallic material reversible to $Na+$ and $K+$ ions.

The membrane preferably is comprised of a three-layer sandwich, the two outer layers being a membrane selectively conducting to $Na+$ and $K+$ ions. The inside layer of the membrane sandwich is of a clay composite permeable to $Na+$ and $K+$ ions and hydrodynamically impermeable.

In the event that the ground water brine includes only primarily $Na+$ or $K+$ ions, then the electrode axis material needs to be reversible only to $Na+$ or $K+$ ions, whichever applies, and the membrane needs to be selectively permeable only to positive ions of $Na+$ or $K+$ ions, whichever applies.

The electrode axis preferably comprises a porous steel substrate and a powdered compound having a soluble and stable crystalline structure of ions of Na+ and K+, or of at least the one that dominates the constituent makeup of the ground water brine at the use location. A preferred cyrstalline structure is selected from a group consisting of $Na_{0.3}TaS_2$ and $K_{0.3}TaS_2$. It should be noted that the "0.3" notation is more accurately "$\frac{1}{3}$".

BRIEF DESCRIPTION OF THE DRAWINGS

So that the manner in which the above-recited features, advantages and objects of the invention, as well as others which will become apparent, are attained and can be understood in detail, more particular description of the invention briefly summarized above may be had by reference to the embodiments thereof that are illustrated in the drawings, which drawings form a part of the specification. It is to be noted, however, that the appended drawings illustrate only preferred embodiments of the invention and are, therefore, not to be considered limiting of its scope for the invention may admit to other equally effective embodiments.

IN THE FIGURES

FIG. 1 is a schematic representation of a side view showing a preferred use of magnetotelluric electrodes in accordance with the present invention.

FIG. 2 is a schematic representation of the top view of the FIG. 1 representation.

FIG. 3 is a schematic representation of a preferred intercalation material employed in the magnetotelluric electrode of the present invention.

FIG. 4 is a schematic representation of ion movement with respect to a preferred material employed in the magnetotelluric material employed in the present invention.

FIG. 5 is a cross-sectional view of a preferred embodiment of a magnetotelluric electrode in accordance with the present invention.

FIG. 6 is a cross-sectional view of a preferred membrane embodiment employed in the magnetotelluric electrode of the present invention.

FIG. 7 is a flow diagram illustrating electron and ion flow in accordance with a preferred embodiment of the present invention.

DESCRIPTION OF PREFERRED EMBODIMENTS

Now referring to the drawings and first to FIG. 1, a survey or study using magnetotelluric electrodes in a field application is shown. Two electrodes 10 and 12 of a type to be more completely described hereafter are inserted, buried or driven into the ground at locations A and B, respectively. Locations A and B are normally in the range of 10 to 5000 feet (3 to 1525 Meters) apart and preferably in the range of 500 to 2000 feet 152 to 610 meters apart. Underneath the ground surface is a formation that is assumed to be very dense and non-porous, such as granite formation 14. Located beneath granite formation 14 is a deposit 16 of hydrocarbons, either oil or gas. Except for the presence of granite formation 14, deposit 16 would be discoverable in a conventional seismic survey. However, because of the nature of layer 14, deposit 16 is virtually non-detectable using conventional seismic techniques. However, it is known that formation 16 is detectable by measuring the naturally appearing voltage at low frequencies below 1 Hz with a voltage sensing element 18 connected above ground to electrodes 10 and 12.

It is known that a natural electromagnetic field 20 at a low frequency below 1 Hz impinges on the surface of the earth at all times and penetrates the surface to a significant depth. By measuring the electrical conductivity or voltage in the manner just described, comparisons will show when there is an oil or gas deposit provided the sensing element is sensitive to very low frequencies, typically, 0.001 Hz, and provided further that noise does not cover up the meaningful information signal. As mentioned previously, not all electrodes are useful if the deposits are very deep because the weak signals that carry the meaningful information are interferred with or covered up by noise.

To achieve even more useful information concerning the oil or gas deposit, assuming that the voltage between electrodes is detectable above the existing noise, it is desirable to detect the voltage between electrode pair 10 and 12 at rotated positions, such as shown in FIG. 2. That is, a first voltage V1 is measured between electrodes 10 and 12. A second voltage V2 is taken at a rotation of 90° from the first measurement line at electrodes 10' and 12'. These electrodes 10' and 12' can be different electrodes of the same design as electrodes 10 and 12 or they can actually be electrodes 10 and 12 at their new respective locations. To make the comparisons meaningful to the maximum degree, the spacing between electrode pairs is the same. Additional electrode placement at other rotation positions are represented by electrodes 10" and 12" and voltage V3.

Although only voltage measuring is described above, the magnetic field perpendicular to line 36 can be measured using appropriate Gauss meter or magnetic field measuring means 19 located near the line. Thus, resistivity of the ground can be calculated by using Ohm's Law for electromagnetic waves, namely, $R \cong V/\beta$. The magnetic field measurement can be made in all of the electrode placements discussed above with respect to FIG. 2 and made contemporaneously with each of the respective voltage measurements previously discussed, thereby producing resistivity measurements for each electrode pair placements.

As previously mentioned, solid metal electrodes capable of use in taking shallow measurements are not satisfactory for deeper measurements because such electrodes are too noisy in operation. At the low frequencies required for taking deep penetration measurements, ions accumulate on the surface of the electrode and form a noisy barrier.

It has long been known in both electrical surveying and seimiconductor physics that it is possible to control the local contact resistance between a solid metal electrode or other object similar thereto and the ground, this control being referred to as "spreading resistance". See for example, L. J. Peters and J. Bardeen, "Some Aspects of Electrical Prospecting Applied in Locating Oil Structures", 2 *Physics*, pp. 103–122 (1932) and W. Shockley, *Electrons and Holes in Semiconductors*, D. VanNostrand Co., N. J., p. 99 (1950).

To better understand spreading resistance, consider the case where a contact is made between two pieces of the same metal. One piece is a large block having an overall dimension of 1 $m^3$. Contact to the block is made with a fine wire etched to a fine point of only one micron in radius. Looking at the total resistance of the point contact and the metal block as series resistors, it is easy to see that the resistance at the point contact is ten million or so times the resistance of the large block and, hence, dominates the overall resistance.

As an example of the expected contact resistance on the earth, consider an electrode of 1 cm radius in a formation of $\rho=100$ ohm-meters resistivity. Spreading resistance, Rs, may be calculated, as follows:

$$Rs = \frac{100}{2\pi \cdot 0.01} = 1600 \text{ ohms}.$$

The total spreading resistance between two such contacts is 3200 ohms. If this contact were made to fresh ground water, the spreading resistance could be ten times larger, leading to a total electrode resistance greater than 10,000 ohms. This resistance is comparable to or larger than antenna resistance typically measured in magnetotelluric applications and shows that the spreading resistance can, in principle, be a large fraction of the total system resistance and, hence, determinative of the noise performance.

The spreading resistance may be reduced by increasing the electrode area, its linear dimensions, or the brine conductivity. One way to reduce spreading resistance is to make the electrode in the shape of a long cylinder. The resistance a distance r from a cylindrical electrode is $R=\rho/2\pi l$), where $\rho$ is the resistivity of the ground and l is the electrode length. Thus the spreading resistance of a cylindrical electrode one meter long and one centimeter in radius would be reduced by a factor of 100 over a similar electrode open or porous only on the end, which is the configuration of a typical cylindrical electrochemical electrode.

FIG. 5 shows the configuration of an electrode in accordance with the present invention that incorporates a structure to obtain low spreading resistance as well as achieving electrochemical reversibility, as hereafter discussed. Outer shell or shield 22 of this electrode is a porous, rigid support for protecting the active elements while allowing electrode contact generally over its entire area, thus utilizing its complete length. Shield 22 is chemically inactive and is conveniently made of a non-biodegradable, hard plastic material.

Inside the shield is a semipermeable membrane 24 that is selectively permeable to Na+ ions, K+ ions or both. The type of desirable membrane is selected to be compatible with the predominant Na and/or K constituent makeup of the brine in the ground water at the location where the electrodes are used. Most brine is predominantly Na in makeup, but there are locations where K predominates and others having significant quantities of both Na and K. The most universally useful membrane is selectively permeable to both Na+ and K+ ions.

Membrane 24 holds an electrolyte 26 for the electrode and is generally NaCl brine or KCl brine or a brine comprising both NaCl and KCl, again dependent on the condition of the brine in the ground water at the location where the electrode is used. A convenient way to obtain a match to the ground water brine is to actually sample and use the in situ ground water brine as the electrolyte.

The electrode axis comprises a porous stainless steel screen or filter cloth 28 encompassing a powder 30 of $Na_xTaS_2$, the intercalation activity of which is illustrated in FIG. 3 and is more completely described below. The electrode is preferably hermetically sealed at the top with cap 32. Electrical contact is made with a solder connection on 34 or an alligator clip or the like to the stainless steel screen or cloth. The contact is attached to a conventional copper or other wire 36 leading to a voltage sensing means, as illustrated in FIG. 1.

The contact is electrically isolated from the other parts of the electrode. Therefore, cap 32 is preferably of the same chemically inactive material as shield 22 or at least the opening of the cap through which screen or cloth 28 protrudes is electrically insulated in any well-known manner. A typical electrode is one meter long and two centimeters in diameter, although the range of length is between six centimeters and two meters and the diameter is in the range between one centimeter and six centimeters.

In operation, the electrode is typically buried in a hole similar to a shot hole, the length of the electrode and depth of the hole being sufficient to place the electrode in contact with the water table.

Now referring to FIG. 6, membrane 24 separates the intercalation electrode axis with its electrolyte from the formation brine to prevent commingling of the brines. The membrane also should be mechanically strong, electronically insulating and stable to temperature variation and acoustic or seismic shock. It will be seen that the membrane structure shown in FIG. 6 is a sandwich-type of structure comprising an outer surface layer 38, an inner surface layer 40, and an enclosed layer 42. Layers 38 and 40 are substantially identical and are a polymeric Na+ or K+ or Na+-and-K+ semipermeable material. The material of polymer membrane layers 38 and 40 permit the passage or conduction of the ions for which they are designed, the design, being dependent on the ground water brine and electrolyte conditions.

Further ion selectivity is achieved by enclosed layer 42, which is preferably a bonded clay composite permeable to Na+, K+ or Na+ and K+ ions. Mica-based clays have recently been studied as Na+-selective membranes by M. S. Whittingham in "Sodium Ion Conduction in Single Crystal Vermiculite", 25 *Solid State Ionics* at page 295 (1987), which is incorporated herein by reference for all purposes. The combined polymer/-clay membrane just described is a highly selective separating membrane that is more selective than a polymer membrane alone and is mechanically robust for application in the electrode previously described.

The major components and interfaces of the intercalation electrode are shown in a block or flow diagram in FIG. 7. There are potentially two major sources of noise in the electrode, namely, thermodynamic noise and current noise. The thermodynamic noise is caused by thermally generated fluctuations in the mobility of conducting ions or electrons, which is described by the fluctuation-dissipation theorem or by the Nyquist Theorem or as Johnson noise. In any event, it is white noise and fairly generally is smaller than the measured noise in magnetotelluric antennas.

The second type of noise is known variously as current noise, flicker noise or diffusion noise and is associated with fluctuations during diffusional transport. Its principal identifying feature is that the voltage or current noise power increases at low frequencies as the reciprocal of the frequency raised to some power typically between 1 and 2. For convenience, such noise can be referred to as "1/f noise". This noise is also proportional to the square of any applied current and is inversely proportional to the number of charge carriers. It is particularly noteworthy that large 1/f noises are observed during diffusion. See M. E. Green, "Diffusion and 1/f Noise", 28 *Journal of Membrane Biol.*, pps. 181-186 (1976). Such noise is also observed during chemical reactions. See G. Feher and M. Weissman, "Fluctuation Spectroscopy: Determination of Chemical Reaction Kinetics from the Frequency Spectrum of Fluctuations", 70 *Proc. Nat. Acad . Sci. USA*, pps. 870-875 (1973). Also, such noise is observed across membranes in concentration cells. See D. L. Dorset and H. M. Fishman, "Excess Electrical Noise During Current Flow Through Porous Membranes Separating Ionic Solutions", 21 *Journal Membrane Biol.*, pps. 291-309 (1975).

Returning to FIG. 7, it is known that in the metallic components of the electrode, the conductivities of the respective members and the number of charge carriers are large. Thus, these components contribute little to overall noise. The other interfaces are potentially cause for troublesome noise.

The $Na_xTaS_2$-NaCl brine interface 44 involves virtual intercalation into and out of the $TaS_2$ material. At this point there is diffusive 1/f noise. However, it will be small in the described electrode because the total area of the powdered $TaS_2$ is very large. Thus, the $Na+$ concentration can be high in both the $Na_xTaS_2$ compound and the brine and the electrochemical potential difference between the $Na+$ in $Na_xTaS_2$ and in NaCl solution is small. The last factor means that ion currents easily flow across the $Na_xTaS_2$-NaCl interface with only a small voltage difference. In contrast, the analogous interface for a $Cu-CuSO_4$ electrode involves a small surface area wire and a change of two electronic charges to remove a $Cu^0$ atom from copper and put it in solution as $Cu^{+2}$. The noise associated with the metal-electrolyte interface should be much smaller in the intercalation electrode. The interfaces between the electrolytes and the membranes all involve noise because the membrane sandwich is not in equilibrium. There will be a continual diffusion across the membrane seeking equilibrium. This diffusion produces 1/f noise. In the usual "pot" electrodes, such as $CuSO_4$, the membrane supports a separation between dissimilar electrolytes. In order for the electrolyte separation to be retained, the separator must have a large resistance to flow of ions because there is a large electrochemical potential difference across the membrane. There is, then, a small number of ions flowing across the membrane, and each ion falls through a large electrochemical potential.

In an intercalation electrode, the electrolytes inside and outside the cell are quite similar so that any electrochemical potential differences are small and the mobility in the membrane is large to produce extremely small membrane noise levels.

A further understanding of the intercalation chemistry that is involved is illustrated in FIG. 3, which illustrates the layered ionic makeup of the $Na_{0.3}TaS_2$ compound. The $TaS_2$ material forms first and second sheets 46 and 48, respectively. A $Na+$ ion 50 is located between sheets 46 and 48 at every third molecule, the other locations being occupied by water. This gives each $Na+$ ion a two dimensional annulus of $H_2O$ that maintains stability of the structure. This material is an excellent ionic conductor that produces a free negative electron each time an $Na+$ ion is displaced, the electron resulting in current flow through the external conductor to the other electrode. This intercalation activity is reversible and with the same movement of $Na+$ ions through the brine in the ground between the electrodes and the membrane materials, there is little noise.

Intercalation compounds that can be used besides $TaS_2$ include any of the alkali-metal-reversible intercalation compounds known to those skilled in the art and specifically including the dichalcogenides of the elements Ti, Zr, Hf, V, Nb, Ta, Cr, Mo and W. Calcogenides include S, Se or Te, the most chemically stable for this application being $TaS_2$ as discussed above, and the most economically desirable being $MoS_2$.

The clay compounds that naturally occur and that are preferably used as material 42 include vermiculite and montmorillonite, although other clays are available.

While a preferred embodiment of the invention has been shown and described, and some modifications or alternatives have been discussed, it will be understood that the invention is not limited thereto since modifications can be made and will become apparent to those skilled in the art. For example, the structure of axis 28 has been described as a screen (like a fine wire screen with warp and woof crossings) or a cloth (which could have random fibers). However, it could be a small cylindrical sieve structure or any other capable of accommodating and accepting therein powder 30. Other similar substitutions can be made throughout, where appropriate.

What is claimed is:

1. The method of magnetotelluric surveying, which comprises
    inserting a first low noise, magnetotelluric, intercalation electrode that is both electronically and ionically conductive and stable in ground water brine into the ground at a first location,
    inserting a second low noise, magnetotelluric, intercalation electrode that is both electronically and ionically conductive and stable in ground water brine into the ground at a second location set apart at a distance from said first location, and
    sensing the voltage therebetween through a connection above ground, said connection joining said first and second electrodes to a voltage indication means sensitive to frequencies below 1 Hz.

2. The method in accordance with claim 1, and including
    newly inserting said first and second electrodes at the same distance apart as said first-named insertions and rotated therefrom, and
    sensing the voltage between said first and second electrodes at said newly inserted locations in the same manner as said first-named sensing.

3. The method in accordance with claim 1, wherein said first and second electrodes are each in the range between approximately 6 centimeters and 2 meters long and have a diameter in the range between approximately 1 centimeter and 6 centimeters.

4. The method in accordance with claim 1, wherein said first and second electrodes are inserted at a distance from each other in the range between approximately 10 feet and 5000 feet.

5. A low noise, magnetotelluric, intercalation electrode that is both electronically and ionically conductive and stable in ground water brine, comprising
    a long cylindrical porous rigid support shield of inactive chemical material,
    a cylindrical semipermeable membrane located within said support shield,
    a brine electrolyte located within said semipermeable membrane, said membrane being selectively permeable to the positive ions of a metal selected from the group consisting of Na+ and K+ ions, and an electrode axis located within said brine electrolyte including an electronically conductive, metallic material ionically reversible to a metal selected from the group consisting of Na+ and K+ for connection to an external electrical contact, said support shield being sealed to enclose therein said membrane, said brine electrolyte, and said electrode axis.

6. A low noise electrode in accordance with claim 5, wherein said support shield has a length in the range between approximately 6 centimeters and 2 meters and a diameter in the range between approximately 1 centimeter and 6 centimeters.

7. A low noise electrode in accordance with claim 6, wherein said support shield is approximately 1 meter long and 2 centimeters in diameter.

8. A low noise electrode in accordance with claim 5, wherein said membrane is mechanically insulating and stable to temperature variation and acoustic shock.

9. A low noise electrode in accordance with claim 5, wherein said membrane is selectively permeable to positive ions of Na+, said membrane comprising a three-layer sandwich, the two outer layers thereof including an Na+— conducting polymer and the inside layer thereof including a clay composite permeable to Na+ ions that is hydrodynamically impermeable.

10. A low noise electrode in accordance with claim 9 wherein said inside layer includes an Na+—selective, mica-based clay.

11. A low noise electrode in accordance with claim 5, wherein said membrane is selectively permeable to positive ions of K+, said membrane comprising a three-layer sandwich, the two outer layers thereof including a K+—conducting polymer and the inside layer thereof including a clay composite permeable to K+ ions that is hydrodynamically impermeable.

12. A low noise electrode in accordance with claim 11, wherein said inside layer includes a K+—selective, mica-based clay.

13. A low noise electrode in accordance with claim 5, wherein said membrane is selectively permeable to positive ions of Na+ and K+, said membrane comprising a three-layer sandwich, the two outer layers thereof including an Na+— and K+—conducting polymer that is hydrodynamically impermeable and the inside layer thereof including a clay composite permeable to Na+ and K+ ions.

14. A low noise electrode in accordance with claim 13, wherein said inside layer includes an Na+—selective and a K+—selective, mica-based clay.

15. A low noise electrode in accordance with claim 5, wherein said brine is NaCl brine.

16. A low noise electrode in accordance with claim 5, wherein said brine is KCl brine.

17. A low noise electrode in accordance with claims 15 or 12, wherein said brine is matched to the formation brine.

18. A low noise electrode in accordance with claim 5, wherein said metallic material included in said axis is reversible to both Na+ and K+.

19. A low noise electrode in accordance with claim 5, wherein said electrode axis comprises a porous steel substrate and a powdered compound having a soluble and stable crystalline structure with ions selected from a group consisting of Na+ and K+.

20. A low noise electrode in accordance with claim 19, wherein said crystalline structure is selected from a group including Na+ ions and K+ ions located between sheets of $TaS_2$.

21. A low noise electrode in accordance with claim 19, wherein said chemical formula for said crystalline structure is selected from a group consisting of $Na_{0.3}TaS_2$ and $K_{0.3}TaS_2$.

22. A low noise electrode in accordance with claim 19, wherein said electrode axis comprises a central stainless steel filter cloth core powdered throughout with powders selected from a group consisting of Na+ reversible, electronically conducting material and K+ reversible, electronically conducting material.

23. A low noise electrode in accordance with claim 22, wherein said powders are powders selected from a group consisting of $Na_xTaS_2$ and $K_xTaS_2$.

* * * * *